US006932972B2

United States Patent
Stephenne et al.

(10) Patent No.: US 6,932,972 B2
(45) Date of Patent: *Aug. 23, 2005

(54) COMBINED VACCINE COMPOSITIONS

(75) Inventors: Jean Stephenne, Rixensart (BE); Martine Anne Cecile Wettendorff, Rhode-Saint-Genese (BE)

(73) Assignee: SmithKline Beecham Biologicals S.A., Rixensart (BE)

( * ) Notice: Subject to any disclaimer, the term of this patent is extended or adjusted under 35 U.S.C. 154(b) by 0 days.

This patent is subject to a terminal disclaimer.

(21) Appl. No.: 10/226,798

(22) Filed: Aug. 23, 2002

(65) Prior Publication Data

US 2003/0129199 A1 Jul. 10, 2003

Related U.S. Application Data

(62) Division of application No. 09/623,708, filed as application No. PCT/EP99/01406 on Mar. 4, 1999, now Pat. No. 6,451,320.

(30) Foreign Application Priority Data

Mar. 9, 1998 (GB) .............................................. 9805105
Jun. 23, 1998 (GB) .............................................. 9813561

(51) Int. Cl.[7] .................... A61K 39/295; A61K 39/395; A61K 39/245; A61K 39/385; A61K 39/42
(52) U.S. Cl. ................ 424/203.1; 424/231.1; 424/226.2; 424/225.1; 424/229.1; 424/227.1; 424/186.1; 424/189.1; 424/279.1; 424/283.1; 530/826
(58) Field of Search ............................ 424/193.1, 225.1, 424/226.1, 227.1, 229.1, 93.1, 231.1, 230, 186.1, 189.1

(56) References Cited

FOREIGN PATENT DOCUMENTS

| EP | 0 339 667 | 4/1989 |
|---|---|---|
| EP | 0 510 996 | 4/1992 |
| WO | WO 92/11291 | 7/1992 |

OTHER PUBLICATIONS

Stanberry et al.N. Eng. J. Med. 2002, vol. 347, No. 21, pp. 1652–1661.*
Constantin et al. Immunotolerance inTexbook of Immunology, 1990, Edited Constantin et al. pp. 170–174.*
Constantin et al. Negative regulation: suppression in Texbook of Immunology, 1990, Edited by Conatantin et al. pp. 255&260.*

* cited by examiner

Primary Examiner—James Housel
Assistant Examiner—Bao Qun Li
(74) Attorney, Agent, or Firm—William P. Majarian; Stephen Venetianer; Charles M. Kinzig

(57) ABSTRACT

Novel combined vaccine composition preferentially for administration to adolescents are provided, comprising a hepatitis B viral antigen and a herpes simplex viral antigen and optionally in addition one or more of the following: an EBV antigen, a hepatitis A antigen or inactivated attenuated virus, an HPV antigen, a V2V antigen, a HCMV antigen, a *Toxoplasma gondii* antigen. The vaccine compositions are formulated with an adjuvant which is a preferential stimulator of TH1 cell response such as 3D-MPL and QS21.

8 Claims, 7 Drawing Sheets

Fig. 1 anti-gD ELISA titers

Fig. 2 anti-HBs ELISA titers

Fig. 3 DTH reaction 24 hrs

Fig. 4 DTH reaction at 48 hrs

Protection Against Primary Disease

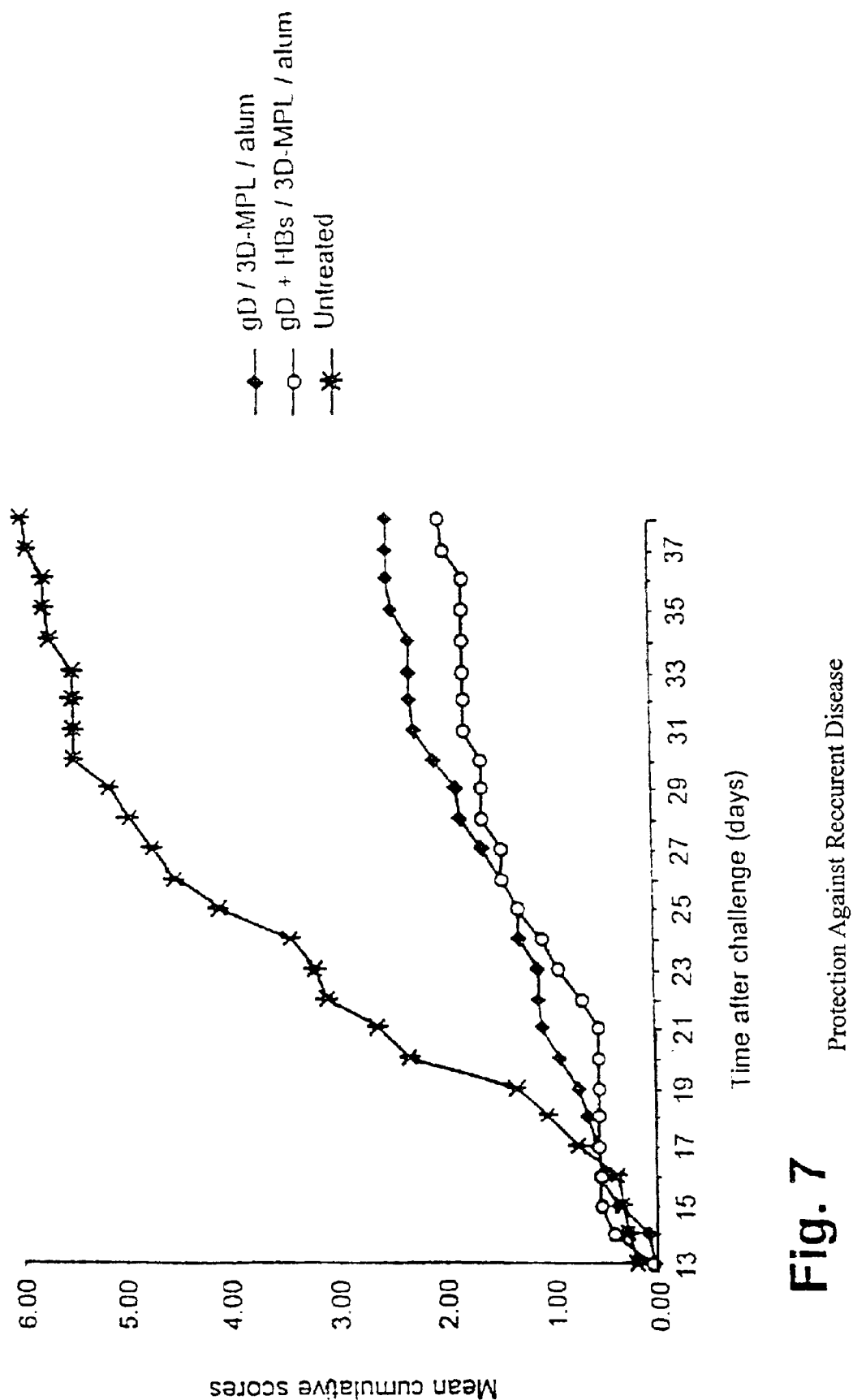
Fig. 7  Protection Against Recurrent Disease

COMBINED VACCINE COMPOSITIONS

This application is a divisional of application Ser. No. 09/623,708, filed Oct. 27, 2000, now U.S. Pat. No. 6,451,320 B1, which was the National Stage of International Application No. PCT/EP99/01406, filed Mar. 4, 1999.

BACKGROUND OF INVENTION

This invention relates to novel vaccine formulations, methods for preparing them and their use in therapy. In particular the present invention relates to combination vaccines for administration to adolescents.

HSV-2 is the primary etiological agent of herpes genitalis. HSV-2 and HSV-1 (the causative agent of herpes labialis) are characterised by their ability to induce both acute diseases and to establish a latent infection, primarily in neuronal ganglia cells.

Genital herpes is estimated to occur in about 5 million people in the U.S.A. alone with 500,000 clinical cases recorded every year (primary and recurrent infection). Primary infection typically occurs after puberty and is characterised by the localised appearance of painful skin lesions, which persist for a period of between 2 to 3 weeks. Within the following six months after primary infection 50% of patients will experience a recurrence of the disease. About 25% of patients may experience between 10–15 recurrent episodes of the disease each year. In immunocompromised patients the incidence of high frequency recurrence is statistically higher than in the normal patient population.

Both HSV-1 and HSV-2 virus have a number of glycoprotein components located on the surface of the virus. These are known as gB, gC, gD and gE etc.

Vaccines for the prophylaxis of hepatitis B infections, comprising one or more hepatitis B antigens, are well known. For example the vaccine Engerix-B (Trade Mark) from SmithKline Beecham Biologicals is used to prevent Hepatitis B. This vaccine comprises hepatitis B surface antigen (specifically the 226 amino acid S-antigen described in Harford et. al. in Postgraduate Medical Journal. 1987, 63 (Suppl. 2), p65–70) and is formulated using aluminium hydroxide as adjuvant.

There is a need for effective combination vaccines to prevent diseases to which adolescents are particularly prone.

SUMMARY OF THE INVENTION

The present invention provides a vaccine composition comprising:
(a) a hepatitis B viral (HBV) antigen; and
(b) a herpes simplex viral (HSV) antigen
in combination with an adjuvant which is a preferential stimulator of TH1 cell response.

The vaccine composition of the invention is of great benefit for administration to adolescents who may be particularly at risk of HBV, and/or HSV infection.

Optionally the vaccine composition of the invention additionally comprises one or more of a number of other antigens as described below.

BRIEF DESCRIPTION OF THE DRAWINGS

FIG. 7. shows that similar numbers of animals have recurrences of a infection in the gD)+HBs and gD alone groups and exactly the same number of animals in these groups has more than 1 recurrence during the observation period (day 13 to 39 post challenge). In those animals with recurrences, the comparable lesion seventies were recorded in both treated and untreated group.

DETAILED DESCRIPTION OF THE INVENTION

Figure 1:
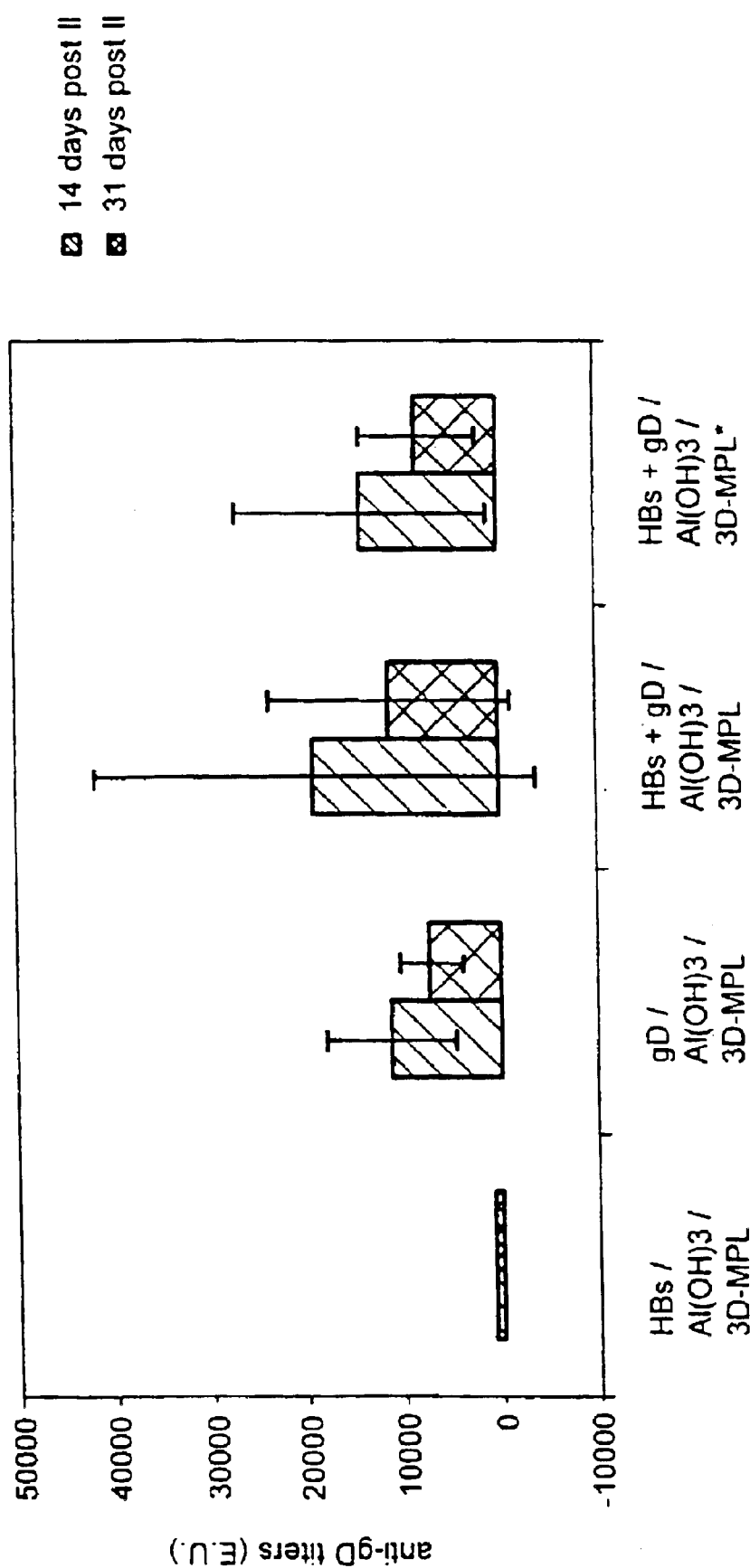
FIG. 1. is Anti-gD ELISA titers.

It has been found that the vaccine compositions according to the invention surprisingly show no interference, that is to say that the immune response to each antigen in the composition of the invention is essentially the same as that which is obtained by each antigen given individually in conjunction with an adjuvant which is a preferential stimulator of TH1 cell response.

The vaccine Havrix (Trade Mark), also from SmithKline Beecham Biologicals is an example of a vaccine that can be used to prevent hepatitis A infections. It is formulated with aluminium hydroxide as adjuvant. This vaccine comprises an attenuated strain of the HM-175 Hepatitis A virus inactivated with formol (formaldehyde); see Andre et. al. (Prog. med. Virol., vol. 37, p1–24).

As used herein, the term hepatitis A viral (HAV) antigen is used to refer to either a protein derived from hepatitis A virus or an attenuated strain of HAV, optionally inactivated, e.g. with formaldehyde. If the HAV antigen is a protein derived from hepatitis A virus it may optionally be a recombinant protein.

The vaccine Twinrix (Trade Mark) is a combination of a recombinant hepatitis B anitgen with the aforementioned inactivated attenuated hepatitis A virus. The vaccine may be used to protect against hepatitis A and hepatitis B simultaneously.

European patent 0 339 667 (Chemo Sero) describes the general concept of combining a hepatitis A antigen and a hepatitis B antigen to make a combination vaccine. In that specification it is stated that the adjuvant which is used is not critical: it must only be capable of enhancing the immune activity to a desired extent and not cause any side-effects. It is stated that aluminium gel may be used, in particular aluminium hydroxide gel and aluminium phosphate gel.

In a further aspect, the invention provides a vaccine composition comprising:
(a) a hepatitis B viral (HBV) antigen;
(b) a herpes simplex viral (HSV) antigen; and
(c) an hepatitis A viral (HAV) antigen
in combination with an adjuvant which is a preferential stimulator of TH1 cell response.

Such a vaccine is of great benefit for administration to adolescents who may be particularly at risk of HBV, and/or HSV infection, and/or HAV infection.

An immune response may be broadly distinguished into two extreme catagories, being a humoral or cell mediated immune responses (traditionally characterised by antibody and cellular effector mechanisms of protection respectively). These categories of response have been termed TH1-type responses (cell-mediated response), and TH2-type immune responses (humoral response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a broad range of immunoglobulin isotypes including in mice IgG1, IgA, and IgM.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute. In reality an individual will support an immune response which is described as being predominantly TH1 or predominantly TH2. However, it is often convenient to consider the families of cytokines in terms of that described in murine CD4+ve T cell clones by Mosmann and Coffman (Mosmann, T. R. and Coffman, R. L. (1989) *TH1 and TH2 cells: different patterns of lymphokine secretion lead to different functional properties. Annual Review of Immunology*, 7, p145–173). Traditionally, TH1-type responses are associated with the production of the INF-$\gamma$ and IL-2 cytokines by T-lymphocytes. Other cytokines often directly associated with the induction of TH1-type immune responses are not produced by T-cells, such as IL-12. In contrast, TH2- type responses are associated with the secretion of IL-4, IL-5, IL-6, IL-10 and tumour necrosis factor-$\beta$(TNF-$\beta$).

It is known that certain vaccine adjuvants are particularly suited to the stimulation of either TH1 or TH2-type cytokine responses. Traditionally the best indicators of the TH 1: TH2 balance of the immune response after a vaccination or infection includes direct measurement of the production of TH1 or TH2 cytokines by T lymphocytes in vitro after restimulation with antigen, and/or the measurement of the IgG1:IgG2a ratio of antigen specific antibody responses.

Thus, a TH1-type adjuvant is one which stimulates isolated T-cell populations to produce high levels of TH1-type cytokines when re-stimulated with antigen in vitro, and induces antigen specific immunoglobulin responses associated with TH1-type isotype.

Adjuvants which are capable of preferential stimulation of the TH1 cell response are described in International Patent Application No. WO 94/00153 and WO 95/17209.

3 De-O-acylated monophosphoryl lipid A (3D-MPL) is one such adjuvant. This is known from GB 2220211 (Ribi). Chemically it is a mixture of 3 De-O-acylated monophosphoryl lipid A with 4, 5 or 6 acylated chains and is manufactured by Ribi Immunochem, Montana. A preferred form of 3 De-O-acylated monophosphoryl lipid A is disclosed in European Patent 0 689 454 B1 (SmithKline Beecham Biologicals SA).

Preferably, the particles of 3D-MPL are small enough to be sterile filtered through a 0.22 micron membrane (as described in European Patent number 0 689 454). 3D-MPL will be present in the range of 10 $\mu$g–100 $\mu$g preferably 25–50 $\mu$g per dose wherein the antigen will typically be present in a range 2–50 $\mu$g per dose.

Another preferred adjuvant comprises QS21, an Hplc purified non-toxic fraction derived from the bark of Quillaja Saponaria Molina. Optionally this may be admixed with 3 De-O-acylated monophosphoryl lipid A (3D-MPL), optionally together with an carrier.

The method of production of QS21 is disclosed in U.S. Pat. No. 5,057,540.

Non-reactogenic adjuvant formulations containing QS21 have been described previously (WO 96/33739). Such formulations comprising QS21 and cholesterol have been shown to be successful TH1 stimulating adjuvants when formulated together with an antigen. Thus vaccine compositions which form part of the present invention may include a combination of QS21 and cholesterol.

Further adjuvants which are preferential stimulators of TH1 cell response include immunomodulatory oligonucleotides, for example unmethylated CpG sequences as disclosed in WO 96/02555.

Combinations of different TH1 stimulating adjuvants, such as those mentioned hereinabove, are also contemplated as providing an adjuvant which is a preferential stimulator of TH1 cell response. For example, QS21 can be formulated together with 3D-MPL. The ratio of QS21:3D-MPL will typically be in the order of 1:10 to 10:1; preferably 1:5 to 5:1 and often substantially 1:1. The preferred range for optimal synergy is 2.5:1 to 1:13D-MPL:QS21.

Preferably a carrier is also present in the vaccine composition according to the invention. The carrier may be an oil in water emulsion, or an aluminium salt, such as aluminium phosphate or aluminium hydroxide.

A preferred oil-in-water emulsion comprises a metabolisible oil, such as squalene, alpha tocopherol and Tween 80. Additionally the oil in water emulsion may contain span 85 and/or lecithin and/or tricaprylin.

In a particularly preferred aspect the antigens in the vaccine composition according to the invention are combined with 3D-MPL and alum.

Typically for human administration QS21 and 3D-MPL will be present in a vaccine in the range of 1 $\mu$g–200 $\mu$g, such as 10–100 $\mu$g, preferably 10 $\mu$g–50 $\mu$g per dose. Typically the oil in water will comprise from 2 to 10% squalene, from 2 to 10% alpha tocopherol and from 0.3 to 3% tween 80. Preferably the ratio of squalene: alpha tocopherol is equal to or less than 1 as this provides a more stable emulsion. Span 85 may also be present at a level of 1%. In some cases it may be advantageous that the vaccines of the present invention will further contain a stabiliser.

Non-toxic oil in water emulsions preferably contain a non-toxic oil, e.g. squalane or squalene, an emulsifier, e.g.

Tween 80, in an aqueous carrier. The aqueous carrier may be, for example, phosphate buffered saline.

A particularly potent adjuvant formulation involving QS21, 3D-MPL and tocopherol in an oil in water emulsion is described in WO 95/17210.

The HSV antigen in the composition of the invention is preferably derived from HSV-2, typically glycoprotein D. Glycoprotein D is located on the viral membrane, and is also found in the cytoplasm of infected cells (Eisenberg R. J. et al; J of Virol 1980, 35, 428–435). It comprises 393 amino acids including a signal peptide and has a molecular weight of approximately 60 kD. Of all the HSV envelope glycoproteins this is probably the best characterised (Cohen et al; J. of Virology, 60, 157–166). In vivo it is known to play a central role in viral attachment to cell membranes. Moreover, glycoprotein D has been shown to be able to elicit neutralising antibodies in vivo (Eing et al J. Med. Virology 127: 59–65). However, latent HSV-2 virus can still be reactivated and induce recurrence of the disease despite the presence of high neutralising antibodies titre in the patients sera.

An embodiment of the invention is a truncated HSV-2 glycoprotein D of 308 amino acids which comprises amino acids 1 through 306 naturally occurring glycoprotein with the addition Asparagine and Glutamine at the C terminal end of the truncated protein devoid of its membrane anchor region. This form of the protein includes the signal peptide which is cleaved to yield a mature 283 amino acid protein. The production of such a protein in Chinese Hamster ovary cells has been described in Genentech's European patent EP-B-139 417.

The recombinant mature HSV-2 glycoprotein D truncate is preferably used in the vaccine formulations of the present invention and is designated rgD2t.

A combination of this antigen in combination with the adjuvant 3D-MPL has been described in WO 92/16231.

The hepatitis B viral (HBV)antigen in the composition of the invention is typically hepatitis B surface antigen.

The preparation of Hepatitis B surface antigen (HBsAg) is well documented. See for example, Harford et. al. in Develop. Biol. Standard 54, page 125 (1983), Gregg et. al. in Biotechnology, 5, page 479 (1987), EP-A-0 226 846, EP-A-0 299 108 and references therein.

As used herein the expression 'Hepatitis B surface antigen', abbreviated herein to 'HBsAg' or 'HBS' includes any HBsAg antigen or fragment thereof displaying the antigenicity of HBV surface antigen. It will be understood that in addition to the 226 amino acid sequence of the HBsAg S antigen (see Tiollais et. al. Nature, 317, 489 (1985) and references therein) HBsAg as herein described may, if desired, contain all or part of a pre-S sequence as described in the above references and in EP-A-0 278 940. HBsAg as herein described can also refer to variants, for example the 'escape mutant' described in WO 91/14703. In a further aspect the HBsAg may comprise a protein described as L* in European Patent Application Number 0 414 374, that is to say a protein, the amino acid sequence of which consists of parts of the amino acid sequence of the hepatitis B virus large (L) protein (ad or ay subtype), characterised in that the amino acid sequence of the protein consists of either:

(a) residues 12–52, followed by residues 133–145, followed by residues 175–400 of the said L protein; or (b) residue 12, followed by residues 14–52, followed by residues 133–145, followed by residues 175–400 of the said L protein.

HBsAg may also refer to polypeptides described in EP 0 198 474 or EP 0 304 578.

Normally the HBsAg will be in particle form. It may comprise S protein alone or may be as composite particles, for example (L*,S) wherein L* is as defined above and S denotes the S-protein of hepatitis B surface antigen.

The HBsAg may be adsorbed on aluminium phosphate as described in WO93/24148.

Preferably the hepatitis B (HBV) antigen used in the formulation of the invention is HBsAg S-antigen as used in the commercial product Engerix-B (Trade Mark; SmithKline Beecham Biologicals).

A vaccine comprising hepatitis B surface antigen in conjunction with 3D-MPL was described in European Patent Application 0 633 784.

Epstein Barr Virus (EBV), a member of the herpesvirus group, causes infectious mononucleosis as a primary disease in humans. Predominantly it affects children or young adults. More than 90% of the average adult population is infected by EBV that persists for lifetime in peripheral B-lymphocytes. The virus is lifelong produced in the parotid gland and spread primarily by exchange of saliva from individuals who shed the virus. Children infected with EBV are largely asymptomatic or have very mild symptoms, while adolescents and adults who become infected develop typical infectious mononucleosis, characterised by fever, pharyngitis, and adenopathy. People who have been infected maintain anti-EBV antibodies for the remainder of their lives, and are thus immune to further infection.

In addition to its infectious qualities, EBV has been shown to transform lymphocytes into rapidly dividing cells and has therefore been implicated in several different lymphomas, including African Burkitt's lymphoma (BL). EBV⁻ may also be involved in causing nasopharyngeal carcinoma (NPC). Worldwide it is estimated that 80,000 cases of nasopharyngeal carcinoma occur and it is more prevalent in ethnic Chinese populations. Infectious mononucleosis is a consequence of primary infection by EBV. It is not a life-threatening disease if additional risk factors are absent.

Four proteins of the EBV viral envelope constituting the so-called membrane antigen complex have been described. They are usually referred to as gp 220/350 or gp 250/350 or simply as gp 250 or 350 (see EP-A-151079). There is convincing evidence that gp 350 and gp 250 induce the production of neutralising antibodies and that antibodies against gp 350 and gp 250 have neutralising capacity. These proteins are thus candidates for a possible EBV vaccine. For further information about the application of gp 250/350 for prophylaxis and treatment of EBV-related diseases see EP 0 173 254.

The major EBV surface glycoprotein gp350/220 infects human target cells through interaction with the cellular membrane protein, CD21. Gp350/220 is the primary target for EBV-neutralising antibodies in humans and some forms of gp350/220 have been shown to protect against EBV-related disease. Preferably a vaccine composition according to the invention comprises gp 350 of EBV although other protective antigens may be used.

Papillomaviruses are small DNA tumour viruses, which are highly species specific. As yet, over 70 individual human papillomavirus (HPV) genotypes have been described. HPVs are generally specific either for the skin (e.g. HPV-1 and -2) or mucosal surfaces (e.g. HPV-6 and -11) and usually cause benign tumours (warts) that persist for several months or years. Such benign tumours may be distressing for the individuals concerned but tend not to be life threatening, with a few exceptions.

Some HPVs are also associated with cancers. The strongest positive association between an HPV and human cancer is that which exists between HPV-16 and HPV-18 and cervical carcinoma. Cervical cancer is the most common malignancy in developing countries, with about 500,000 new cases occurring in the world each year. It is now technically feasible to actively combat primary HPV-16 infections, and even established HPV-16-containing cancers, using vaccines. For a review on the prospects for prophylactic and therapeutic vaccination against HPV-16 see Cason J., Clin. Immunother. 1994; 1(4) 293–306 and Hagenesee M. E., Infections in Medicine 1997 14(7) 555–556,559–564. Preferably a vaccine composition according to the invention comprises the major capsid protein, the L1 protein.

Today, the different types of HPVs have been isolated and characterised with the help of cloning systems in bacteria and more recently by PCR amplification. The molecular organisation of the HPV genomes has been defined on a comparative basis with that of the well characterised bovine papillomavirus type 1 (BPV1).

Although minor variations do occur, all HPVs genomes described have at least seven early genes, E1 to E7 and two late genes L1 and L2. In addition, an upstream regulatory region harbors the regulatory sequences which appears to control most transcriptional events of the HPV genome.

E1 and E2 genes are involved in viral replication and transcriptional control, respectively and tend to be disrupted by viral integration. E6 and E7, and recent evidence implicate also E5 are involved in viral transformation.

In the HPVs involved in cervical carcinoma such as HPV 16 and 18, the oncogenic process starts after integration of viral DNA. The integration results in the inactivation of genes coding for the capsid proteins L1 and L2 and in installing continuously over expression of the two early proteins E6 and E7 that will lead to gradually loss of the normal cellular differentiation and the development of the carcinoma.

Carcinoma of the cervix is common in women and develops through a pre-cancerous intermediate stage to the invasive carcinoma which frequently leads to death. The intermediate stages of the disease is known as cervical intraepithelial neoplasia and is graded I to III in terms of increasing severity.

Clinically, HPV infection of the female anogenital tract manifests as cervical flat condylomas, the hallmark of which is the koilocytosis affecting predominantly the superficial and intermediate cells of the cervical squamous epithelium.

Koilocytes which are the consequence of a cytopathic effect of the virus, appear as multinucleated cells with a perinuclear clear halo. The epithelium is thickened with abnormal keratinisation responsible for the warty appearance of the lesion.

Such flat condylomas when positive for the HPV 16 or 18 serotypes, are high-risk factors for the evolution toward cervical intraepithelial neoplasia (CIN) and carcinoma in situ (CIS) which are themselves regarded as precursor lesions of invasive cervix carcinoma.

International Patent Application No. WO 96/19496 discloses variants of human papilloma virus E6 and E7 proteins, particularly fusion proteins of E6/E7 with a deletion in both the E6 and E7 proteins. These deletion fusion proteins are said to be immunogenic.

HPV L1 based vaccines are disclosed in WO94/00152, WO94/20137, WO93/02184 and WO94/05792. Such a vaccine can comprise the L1 antigen as a monomer, a capsomer or a virus like particle. Such particles may additionally comprise L2 proteins. Other HPV vaccines are based on the Early proteins, such as E7 or fusion proteins such as L2-E7.

In the vaccine of the invention it is preferred to utilise compositions comprising either an E6 or E7 protein linked to an immunological fusion partner having T cell epitopes.

In a preferred form of the invention, the immunological fusion partner is derived from protein D of Heamophilus influenza B. Preferably the protein D derivative comprises approximately the first ⅓ of the protein, in particular approximately the first N-terminal 100–110 amino acids.

Accordingly the present invention in one embodiment comprises antigen (s) derived from HPV as described above. Preferably the invention comprises fusion proteins comprising Protein D-E6 from HPV 16, Protein D-E7 from HPV 16 Protein D-E7 from HPV 18 and Protein D-E6 from HPV 18. The protein D part preferably comprises the first ⅓ of protein D.

The proteins of the present invention preferably are expressed in *E. coli*. In a preferred embodiment the proteins are expressed with a Histidine tail comprising between 5 to 9 and preferably six Histidine residues. These are advantageous in aiding purification. The description of the manufacture of such proteins is fully described in co-pending UK patent application number GB 9717953.5.

In a preferred aspect the vaccine composition of the invention additionally comprises a Varicella Zoster viral antigen (VZV antigen). Suitable antigens of VZV for inclusion in the vaccine formulation include gpI-V described by Longnecker et al., Proc Natl Acad Sci USA 84, 4303–4307 (1987).

In a preferred embodiment gpI (see Ellis et al., U.S. Pat. No. 4,769,239) is used. See also European Patent No. 0 405 867 B1.

In another preferred aspect the vaccine composition of the invention additionally comprises a human cytomegalovirus (HCMV) antigen. HCMV is a human DNA virus belonging to the family of herpes viruses. HCMV is endemic in most parts of the world. Among two populations, HCMV is responsible for serious medical conditions. HCMV is a major cause of congenital defects in new borns. The second population at risk are immunocompromised patients such as those suffering from HIV infection and those patients undergoing transplantations. The clinical disease causes a variety of symptoms including fever, hepatitis, pneumonitis and infectious mononucleosis. A preferred antigen for use in a vaccine against HCMV is gB685** as described in WO 95/31555. immunogens for use in HCMV vaccines are also provided by pp65, an HCMV Matrix Protein as described in WO 94/00150 (City of Hope).

In one preferred aspect the vaccine composition of the invention additionally comprises both a VZV and an HCMV antigen, in particular those antigens described above.

In another preferred aspect the vaccine composition of the invention additionally comprises a *Toxoplasma gondii* antigen. *Toxoplasma gondii* is an obligate intracellular protozoan parasite responsible for toxoplasmosis in warm-blooded animals, including man. Although it is generally clinically asymptomatic in healthy individuals, toxoplasmosis may cause severe complications in pregnant women and immunocompromised patients. A preferred antigen for use in a vaccine against *Toxoplasma gondii* is SAG1 (also known as P30) as described in WO96/02654 or Tg34 as described in WO92/11366.

In one preferred aspect the vaccine composition of the invention additionally comprises either a VZV antigen or an HCMV antigen combined with a *Toxoplasma gondii* antigen, in particular those antigens described above.

In a preferred aspect the vaccine composition of the invention is a multivalent vaccine, for example a tetra- or pentavalent vaccine.

The formulations of the present invention are very effective in inducing protective immunity, even with very low doses of antigen (e.g. as low as 5 μg rgD2t).

They provide excellent protection against primary infection and stimulate, advantageously both specific humoral (neutralizing antibodies) and also effector cell mediated (DTH) immune responses.

The present invention in a further aspect provides a vaccine formulation as herein described for use in medical therapy, particularly for use in the treatment or prophylaxis of Herpes Simplex infections and hepatitis B viral infections.

The vaccine of the present invention will contain an immunoprotective quantity of the antigens and may be prepared by conventional techniques.

Vaccine preparation is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed. Generally, it is expected that each dose will comprise 1–1000 μg of protein, preferably 2–100 μg, most preferably 440 μg. An optimal amount for a particular vaccine can be ascertained by standard studies involving observation of antibody titres and other responses in subjects. Following an initial vaccination, subjects may receive a boost in about 4 weeks.

In addition to vaccination of persons susceptible to HSV or HBV viral infections, the pharmaceutical compositions of the present invention may be used to treat, immunotherapeutically, patients suffering from the said viral infections.

In a further aspect of the present invention there is provided a method of manufacture as herein described, wherein the method comprises mixing a herpes viral antigen and a hepatitis B viral antigen with a TH-1 inducing adjuvant, for example 3D-MPL and, preferably, a carrier, for example alum.

If desired, other antigens may be added, in any convenient order, to provide multivalent vaccine compositions as described herein.

EXAMPLES

Example 1

Immunogenicity Study with gD+HBs Combination

The objective of the study was to demonstrate the feasibility of the HSV gD/HBV HBs combination in $Al(OH)_3$/3D-MPL formulation. Immune responses induced in guinea pigs by immunisation with these antigens used alone or in combination were compared. HBs is an abbreviation for Hepatitis B surface antigen, specifically the S-protein as described hereinabove. gD is an abbreviation for $rgD_2t$ as described hereinabove.

Experimental Protocol

The experimental protocol was the following. Groups of 6 female Hartley guinea pigs were injected intramuscularly on day 0 and day 28 with the following formulations:
group 1: HBs 5 μg/$Al(OH)_3$ 125 μg/3D-MPL 12.5 μg
group 2: gD 5 μg/$Al(OH)_3$ 125 μg/3D-MPL 12.5 μg
group 3: HBs 5 μg+gD 5 μg/$Al(OH)_3$ 125 μg/3D-MPL 12.5 μg
group 4: HBs 5 μg+gD 5 μg/$Al(OH)_3$ 125 μg/3D-MPL* 12.5 μg
* different 3D-MPL batch Animals were bled 14 and 31 days after the second immunization. The humoral immune response against HSV gD and HBV HBs was evaluated at both time points in ELISA.

Delayed type hypersensitivity (DTH) reactions were also evaluated for HBs. They consisted in the intradermal injection of 10 μg HBs in duplicate. The development of DTH reactions was monitored by measuring skin thickness at 0, 24 and 48 hours after injection.

Results

1. Antibody Responses

Anti-gD ELISA titers are shown in FIG. 1. Anti-gD titers in the group immunized with gD were comparable to those induced in animals immunized with the gD+HBs combination. The presence of HBs in the formulation did not affect the induction of anti-gD antibody responses.

Figure 2:
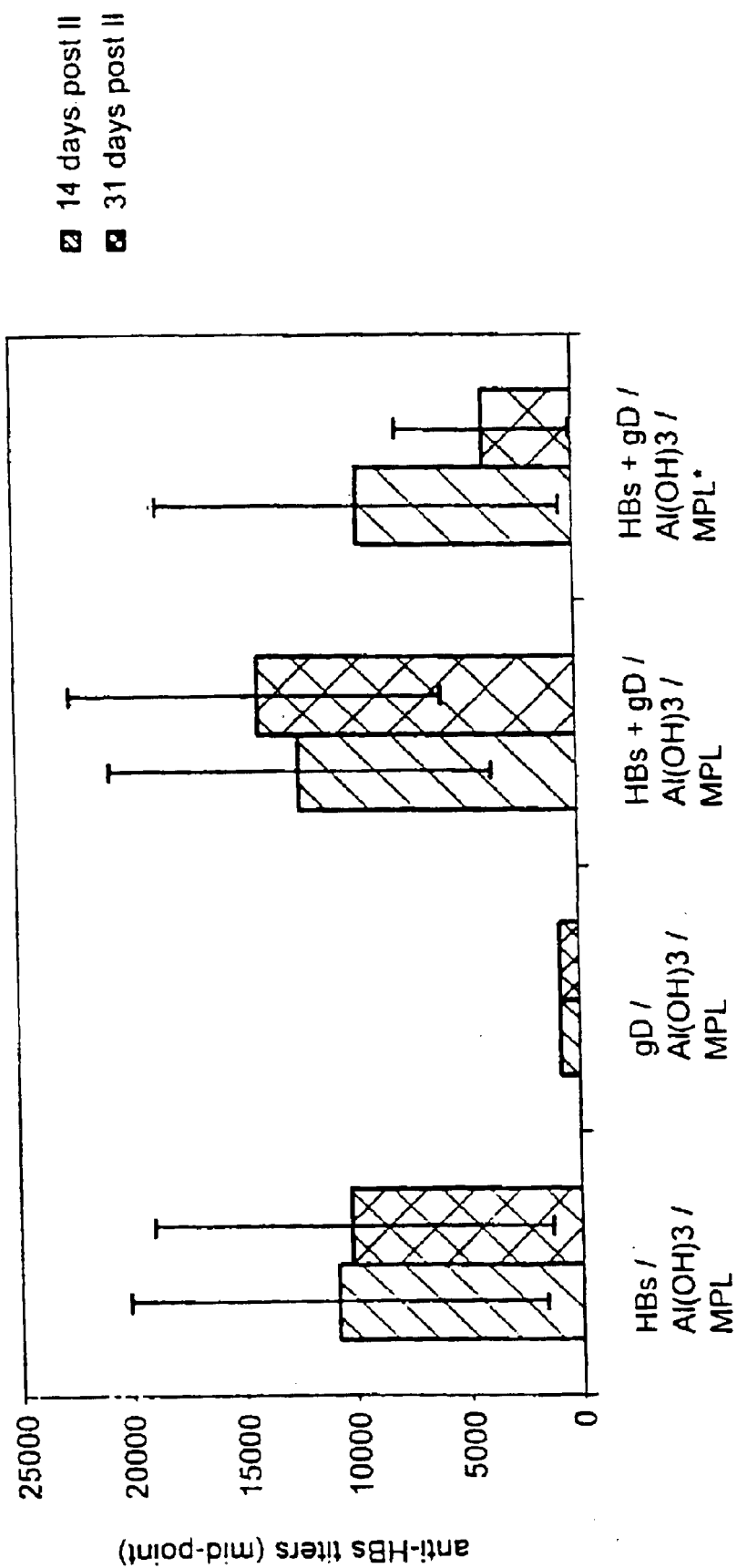
FIG. 2. is Anti-HBs ELISA titers.
Figure 3:
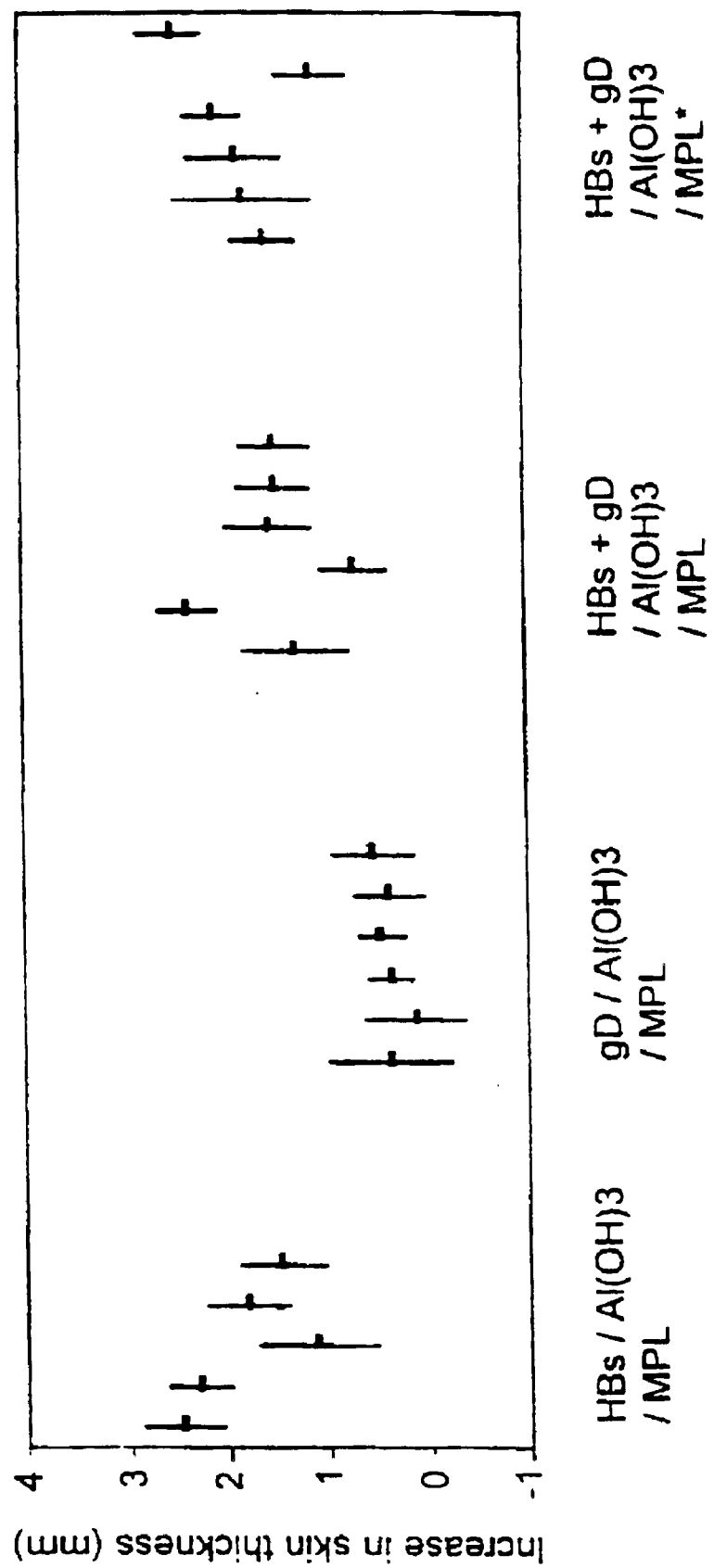
FIG. 3. is DTH reaction at 24 hrs.
Figure 4:
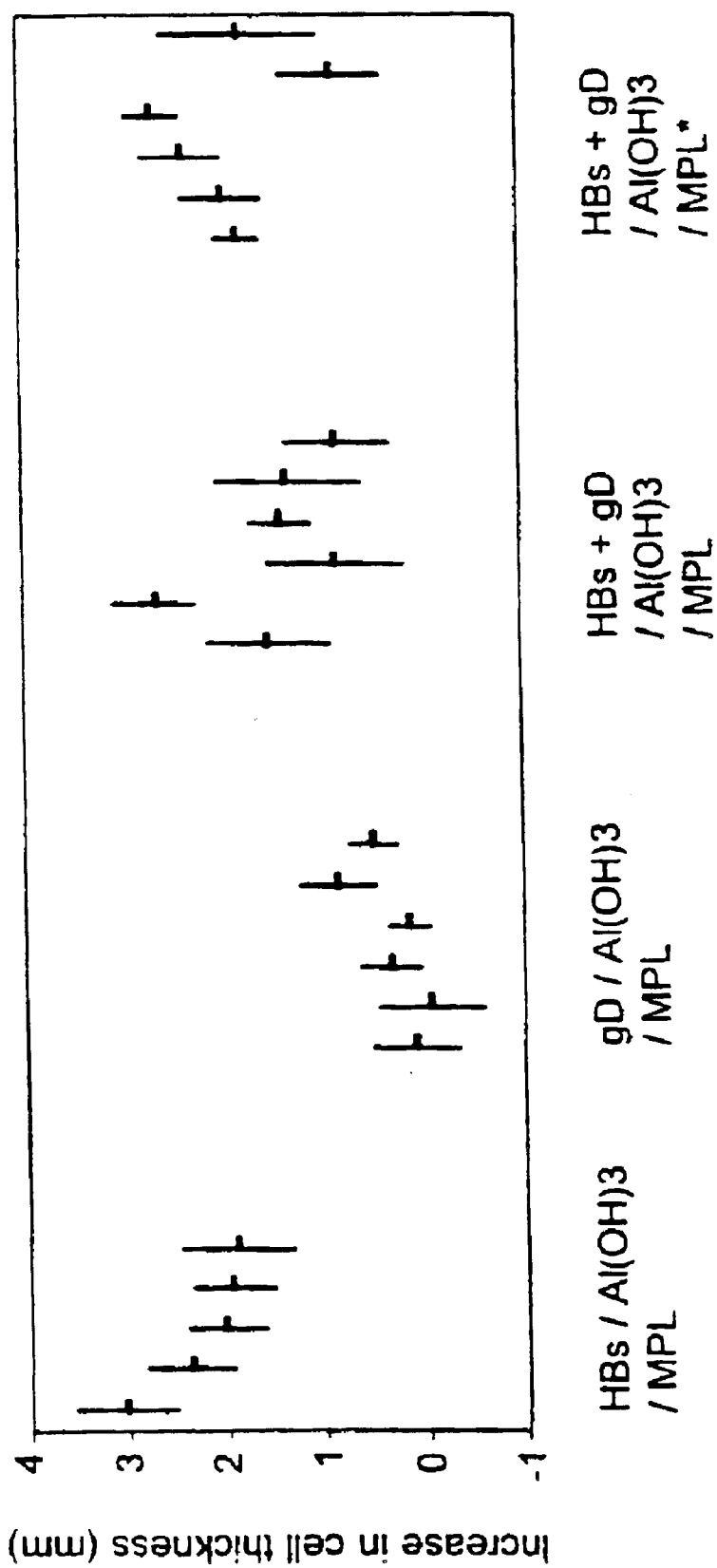
FIG. 4. is DTH reaction at 48 hrs.

Similarly, anti-HBs antibody titers were compared in animals immunized with HBs alone or combined with gD. FIG. 2 shows that comparable anti-HBs titers were observed in animals immunized with HBs alone or with HBs+gD.

The results are shown in FIGS. 1–4 from which it may be concluded that in the tested formulation, the gD/HBs combination induces antibody responses comparable to those induced by the same antigens used alone and DTH responses to HBs comparable to those induced by HBs alone. Thus no significant differences in DTH responses to HBs are observed in HBs or HBs+gD vaccinated animals. The presence of gD did not affect the DTH response to HBs.

Example 2

PRO30 Experiment HBV/HSV Combination

The objective of this study was to evaluate in the HSV guinea pig model the protective efficacy of an HSV gD+HBV HBs combination in a 3D-MPL/alum formulation as compared to gD alone in a 3D-MPL/alum formulation. The 3D-MPL/alum formulation comprises alum (10 parts by weight) to 3D-MPL (1 part by weight).

Experimental Protocol

Groups of twelve females Hartley guinea pigs were immunized with the following formulations or left untreated:

| | | | |
|---|---|---|---|
| gD + HBs/3D-MPL/alum formulation | gD (5 µg) + HBs (5 µg) | Al(OH)3, (62.5 µg) + Al(OH)3, (62.5 µg) | 3D-MPL (6.25 µg) + 3D-MPL (6.25 µg) |
| gD/3D-MPL/alum formulation | gD (5 µg) | Al(OH)3, (125 µg) | 3D-MPL (12.5 µg) |

Animals were immunized intramuscularly twice at days 0 and 28. They were intravaginally challenged at day 57 (1 month after the second immunization) with $10^5$ pfu HSV2 MS strain (100 µl) and then daily monitored for clinical signs of primary (days 4 to 12 post-infection) and recurrent (days 13 to 39 post-infection) disease. The protection induced was measured according to several criteria described in Table 1, as well as by cumulative score curves.

Sera collected at days 14 and 28 post II immunization were also tested for their anti-gD ELISA Ab titers (expressed as EU/ml); sera obtained at day 28 post II were also tested for their HSV neutralizing activity ('NEUTRA'; titers correspond to the reciprocal of the serum dilution giving 100% protection against HSV2 cytopathic effect).

Results

Figure 5:
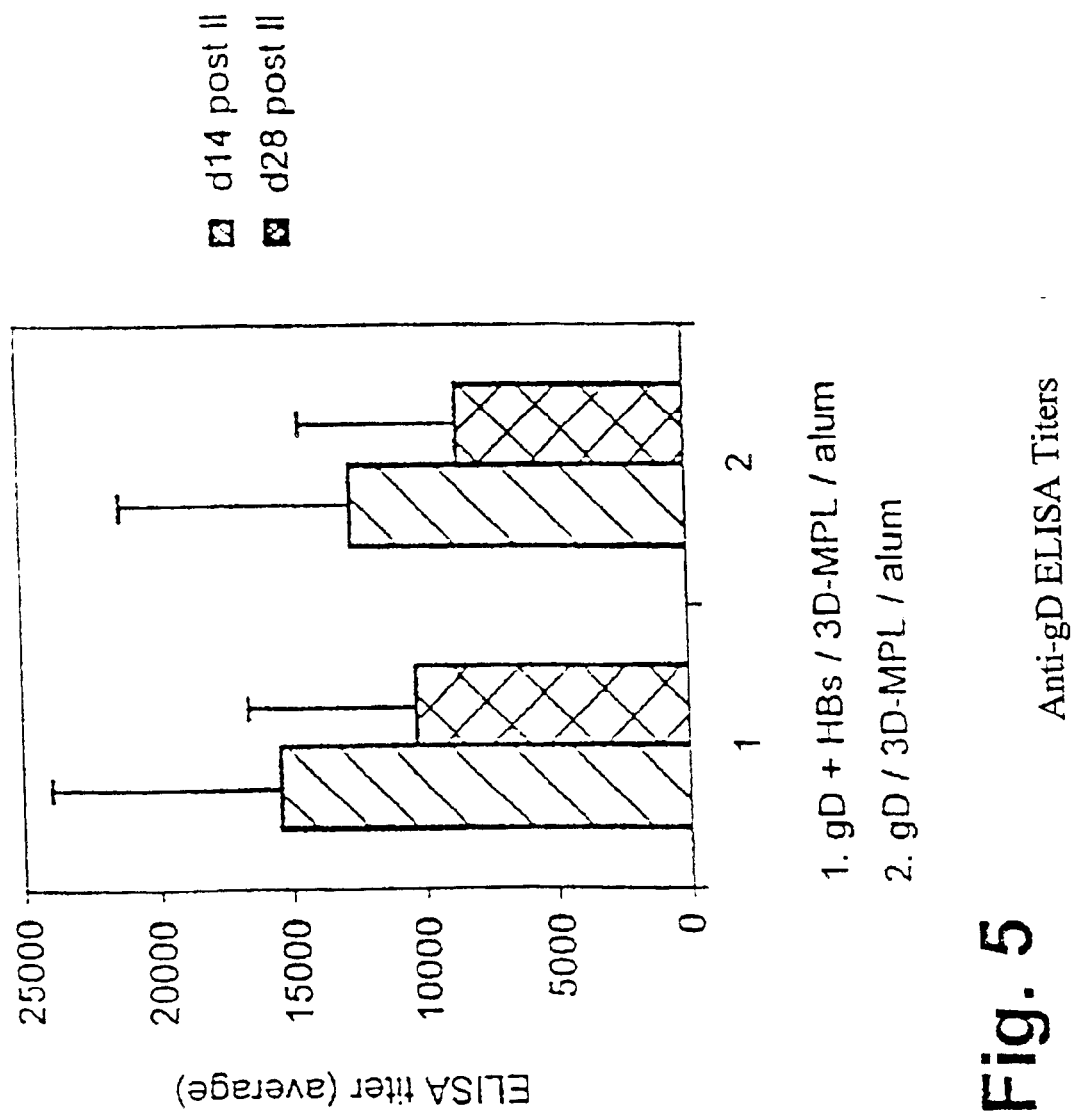
FIG. 5. shows similar ELISA and neutralizing titers induced by the gD (5ug)+HBs (5ug) combination in 3D-MPL/alum and gD/3D-MPL/alum.

Serology Results:

Immunogenicity data are presented in the following Table and FIG. 5:

| | Neutra/ELISA ratio at days 28 post II | | |
|---|---|---|---|
| FORMULATIONS | ELISA (GMT) | NEUTRA (GMT) | Ratio NEUTRA/ELISA |
| gD + HBs/3D-MPL/alum formulation | 6687 | 238 | 3.5% |
| gD/3D-MPL/alum formulation | 7475 | 200 | 2.7% |

Similar ELISA and neutralizing titers were induced by the gD (5 µg)+HBs (5 µg) combination in 3D-MPL/alum formulation and gD/3D-MPL/alum formulation.

Figure 6:
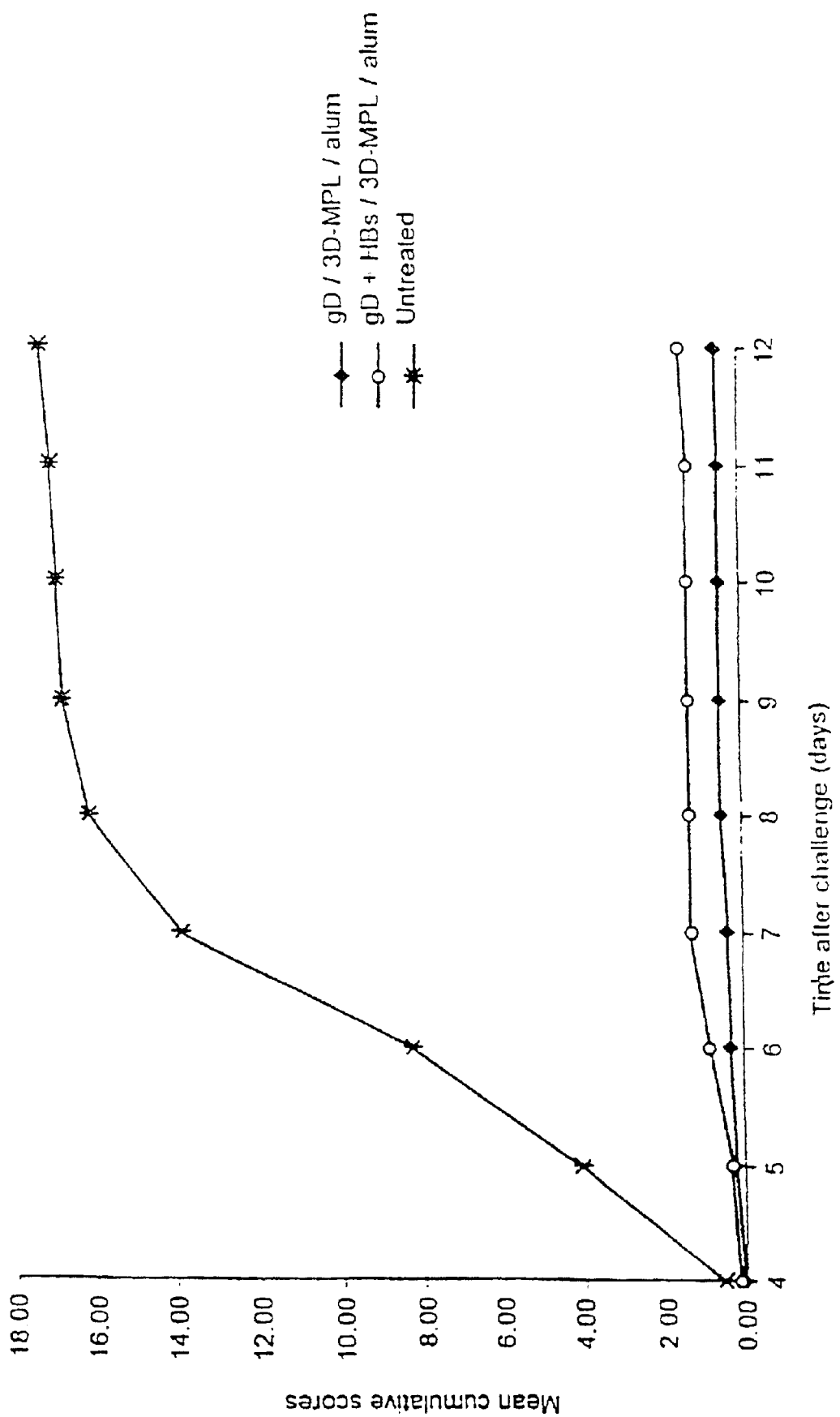
FIG. 6. shows that both guinea pigs immunized with the gD+HBs combination and gD alone are very well protected against HSV challenge. While most control animals had lesions. These were observed in respectively 2/12 and 3/12 animals only in the gD+HBs and gD alone groups.

Protection Against Primary Disease:

As shown in FIG. 6 (cumulative score curve) and in Table 1 below, gD+HBs/3D-MPL/alum formulation combination conferred as good protection against primary disease as gD alone in 3D-MPL/alum formulation.

Protection Against Recurrent Disease:

Protection against herpes recurrences is shown in FIG. 7 (cumulative score curves) and in Table 2 below. gD+HBs/3D-MPL/alum formulation combination conferred as good protection against recurrent disease as gD alone in 3D-MPL/alum formulation.

Similar number of animals had recurrences in the gD+HBs and gD alone groups. Exactly the same number of animals in these groups had more than 1 recurrence during the observation period (day 13 to 39 post challenge). In those animals with recurrences, comparable lesion severity were recorded.

TABLE 1

Primary Disease

| | | | | Vaginal Lesions | External lesions | | Lesion severity * | | |
|---|---|---|---|---|---|---|---|---|---|
| GROUP | n | FORMULATION | Animal without lesion | Incidence % | Incidence % | PI index** | median | % vs control | n |
| 1 | 12 | gD/3D-MPL/alum | 75.0 | 16.7 | 8.3 | 25.0–96% | 0.50 | −96% | 3 |
| 2 | 12 | gD + HBs/3D-MPL/alum | 83.3 | 0.0 | 16.7 | 50.0–91% | 9.00 | −22% | 2 |
| 3 | 12 | Untreated | 16.7 | 8.3 | 75.0 | 587.5 | 11.50 | | 10 |

\* Sum of the lesion scores for the days 4', to 12 post-infection (animals without lesion are considered).
Lesion scores: no lesion (0), vaginal lesions (0.5 or 1), external skin vesicles (2, 4, 8 or 16)
\*\*Primary infection index = sum (Max.score i) × (Incidence %); with i = 0, 0.5, 1, 2, 4, 8 or 16

TABLE 2

Recurrent Disease

RECURRENT DISEASE

| | | Animals w/o rec. | | Animals with recurrence | | | | Lesion Severity * | | | |
|---|---|---|---|---|---|---|---|---|---|---|---|
| | | With PI | | w/o PI | With P.I. | Total | More than 1 | | % vs | | Duration |
| n | FORMULATION | incidence % | Total % | Incidence % | Incidence % | lesion % | recurrence % | Median | control | n | Median | n |
| 12 | gD/3D-MPL/alum | 8.3 | 58.3 | 25.0 | 16.7 | 41.7 | 16.6 | 3.00 | −57% | 5 | 4.00 | 5 |
| 12 | gD + HBs/3D-MPL/alum | 8.3 | 66.7 | 25.0 | 8.3 | 33.3 | 16.6 | 5.50 | −21% | 4 | 3.50 | 4 |
| 12 | Untreated | 8.3 | 25.0 | 0.0 | 75.0 | 75.0 | 50 | 7.00 | | | 6.00 | 9 |

Both guinea pigs immunized with the gD + HBs combination and guinea pigs immunized with gD alone were very well protected against HSV challenge. While most control animals had lesions, these were observed in respectively 2/12 and 3/12 animals only in the gD + HBs and gD alone groups.

Example 3

The objective of the study is to evaluate the serological immune responses induced in mice by a combination vaccine comprising HAV, HBs and gD formulated with Aluminium salts and 3D-MPL. The hepatitis A component used in this example (and abbreviated herein to 'HAV') was the inactivated HM175 strain found in Havrix.

Materials and Methods

Antigen/3D-MPL Batches:

HBs: Al:4550 µg/ml, pre-adsorbed HBs: 227,62 µg/ml
HAV: Al: 1380 µg/ml, HAV:25230 EU/ml
gD: 493 µg/ml
3D-MPL: 957 µg/ml Formulation Process Group 1: HBs $AlPO_4$/3D-MPL HBs/$H_2O$/NaCl/phenoxy/$AlPO_4$ for 15 min+3D-MPL for 1 hr Group 2: gD $AlOH_3$/3D-MPL H2O/$AlOH_3$ for 5 min+gD for 15 min+3D-MPL for 30 min+PBS for 15 min+Phenoxy Group 3: HAV $AlOH_3$/3D-MPL $H_2O$/NaCl/Phenoxy for 5 min+$AlOH_3$/HAV for 30 min/3D-MPL Group 4:
1. $H_2O$/NaCl/Phenoxy for 5 min+$AlPO_4$/HBs for 5 min+3D-MPL 30 min
2. gD/$AlOH_3$ for 15 min+3D-MPL for 30 min
Mix 1 and 2 for 20 min+HAV for 1 hr.

Serological Read-Outs

Quantitation of anti-HBs and anti-gD antibody was performed by Elisa using HBs or gD as coating antigen. Antigen and antibody solutions were used at 50 µl per well. Antigen was diluted at a final concentration of 1 µg/ml in PBS and was adsorbed overnight at 4° c. to the wells of 96 wells microtiter plates (Maxisorb Immunoplate, Nunc, Denmark). The plates were then incubated for 1 hr at 37° c. with PBS containing 1% bovine serum albumin and 0.1% Tween 20 (saturation buffer). Two-fold dilutions of sera in the saturation buffer were added to the antigen-coated plates and incubated for 1 hr 30 min at 37° c. The plates were washed four times with PBS 0.1% Tween 20 and biotin-conjugated anti-mouse Ig (Amersham, UK) diluted 1/1000 in saturation buffer was added to each well and incubated for 1 hr 30 min at 37° c. After a washing step, streptavidin-biotinylated peroxydase complex (Amersham, UK) diluted 1/5000 or 1/1000 in saturation buffer (for HBs and anti-gD ELISA respectively) was added for an additional 30 min at 37° c. Plates were washed as above and incubated for 20 min with a solution of o-phenylenediamine (Sigma) 0.04% $H_2O_2$ 0.03% in 0.1% tween 20 0.05M citrate buffer pH 4.5. The reaction was stopped with $H_2SO_4$ 2N and read at 492/620 nm. ELISA titers were calculated from a reference by SoftmaxPro (using a four parameters equation) and expressed in EU/ml.

Quantitation of anti-HAV antibody was performed by Enzymun ELISA (Boehringer) according to Manufacturer's protocol.

Experimental Protocol

Groups of 7 Balb/C mice were immunised intramuscularly with the following formulations (corresponding to 1/10 human dose):

1. HBs (2 µg)/AlPO4 (50 µg)/3D-MPL (5 µg)
2. gD (2 µg)/Al(OH)3 (50 µg)/3D-MPL (5 µg)
3. HAV (72EU)/Al(OH)3 (50 µg)/3D-MPL (5 µg)
4. HAV (72U)/Al(OH)3 (5 µg)+HBs (2 µg)/AlPO4 (40 µg)/3D-MPL (2.5 µg)+gD (2 µg)/Al(OH)3 (5 µg)/3D-MPL(2.5 µg)

Animals were immunised twice at day 0 and 21 with 50 µl vaccine. Sera were collected at various time points post-immunisations (21 post I and 14 post II) and were tested for their anti-HAV, HBs and gD antibody titers.

Results

Individual data from 21 post I and 14 post II are shown in Table 3 and summarised below:

TABLE 3

| | Anti HBs response (EU/ml) | | Anti-HAV response (mIU/ml) | | Anti-gD response (EU/ml) | |
|---|---|---|---|---|---|---|
| | | | 14 post | | | |
| | 14 post I | II | 14 post I | II | 14 post I | 14 post II |
| Gr.1 DHB56A2: HBs 20/PO4/3D-MPL 50 | | | | | | |
| | 659 | 127282 | | | | |
| | 935 | 165796 | | | | |
| | 979 | 118574 | | | | |
| | 934 | 55063 | | | | |
| | 1606 | 102040 | | | | |
| | 879 | 90388 | | | | |
| | 409 | 39447 | | | | |
| GMT | 880 | 75015 | | | | |
| Gr.2 gD 20/OH/3D-MPL 50 | | | | | | |
| | | | | | 989 | 149616 |
| | | | | | 1150 | 97672 |

TABLE 3-continued

| | Anti HBs response (EU/ml) | | Anti-HAV response (mIU/ml) | | Anti-gD response (EU/ml) | |
|---|---|---|---|---|---|---|
| | 14 post I | 14 post II | 14 post I | 14 post II | 14 post I | 14 post II |
| | | | | | 564 | 61866 |
| | | | | | 1087 | 100172 |
| | | | | | 805 | 73340 |
| | | | | | 1135 | 186113 |
| | | | | | 598 | 122633 |
| GMT | | | | | 871 | 106123 |
| Gr.3 HAV 720/OH/3D-MPL 50 | | | | | | |
| | | | 20 | 20 | | |
| | | | 20 | 20 | | |
| | | | 20 | 41 | | |
| | | | 20 | 20 | | |
| | | | 20 | 37 | | |
| | | | 20 | 20 | | |
| | | | 20 | 20 | | |
| GMT | | | 20 | 25 | | |
| Gr.4 HAV 720/OH-HBs 20/PO4/3D-MPL 25 - gD 20/OH/3D-MPL 25 | | | | | | |
| | 88 | 63427 | 25 | 272 | 202 | 61711 |
| | 336 | 72765 | 20 | 28 | 1166 | 105676 |
| | 395 | 78781 | 20 | 498 | 730 | 65277 |
| | 474 | 99881 | 20 | 380 | 819 | 62107 |
| | 890 | 112439 | 20 | 20 | 395 | 76378 |
| | 542 | 120652 | 20 | 20 | 493 | 54908 |
| | 1020 | 41460 | 20 | 20 | 345 | 35466 |
| GMT | 414 | 79699 | 21 | 91 | 549 | 69312 |

HBs serology

| | Anti-HBs ELISA titers (EU/ml) | |
|---|---|---|
| Group | Post I | Post II |
| HBs AlPO4 3D-MPL | 880 | 75015 |
| HAV Al(OH)3/HBs AlPO4 3D-MPL/gD Al(OH)3 3D-MPL | 414 | 79699 | gD serology

| | Anti-gD ELISA titers (EU/ml) | |
|---|---|---|
| Group | Post I | Post II |
| gD Al(OH)3 3D-MPL | 871 | 106123 |
| HAV Al(OH)3/HBs AlPO4 3D-MPL/gD Al(OH)3 3D-MPL | 549 | 69312 |

HAV serology

| | Anti-HAV ELISA titers (mIU/ml) | |
|---|---|---|
| Group | Post I | Post II |
| HAV Al(OH)3 3D-MPL | 20 | 25 |
| HAV Al(OH)3/HBs AlPO4 3D-MPL/gD Al(OH)3 3D-MPL | 21 | 91 |

CONCLUSIONS

Comparable anti-HBs antibody titers in the combination vaccine and in HBs vaccine containing Aluminium salts and 3D-MPL were observed.

Comparable anti-gD antibody titers in the combination vaccine and in gD vaccine containing Aluminium salts and 3D-MPL were observed.

Comparable anti-HAV antibody titers in the combination vaccine and in HAV vaccine containing Aluminium salts and 3D-MPL were observed.

Thus there appears to be no interference when HBs, gD and HAV are combined in a vaccine containing aluminium salts and 3D-MPL.

What is claimed is:

1. A vaccine composition comprising:

(a) a hepatitis B surface antigen (HBsAg) for inducing an immunoprotective response; and (b) a herpes simplex glycoprotein D (HSV gD) antigen or a truncate thereof, wherein the truncate comprises amino acids 1–306 of a naturally occuring glycoprotein D, for inducing an immunoprotective response, in conjunction with an adjuvant which is a preferential stimulator of TH 1 cell response wherein the HBsAg antigen and the HSV gD antigen are not covalently linked to each other.

2. A vaccine composition according to claim 1 which additionally comprises a carrier.

3. A vaccine composition according to claim 1 or claim 2 in which the preferential stimulator of TH1-cell response is selected from the group of adjuvants comprising: 3D-MPL, 3D-MPL wherein the size of the particles of 3D-MPL is preferably about or less than 100 nm, QS21, a mixture of QS21 and cholesterol, and a CpG oligonucleotide.

4. A vaccine composition according to claim 3 in which the preferential stimulator of TH1-cell response is 3D-MPL.

5. A vaccine composition according to claim 1 or claim 2 in which a hepatitis A antigen for inducing an immunoprotective response is additionally present.

6. A vaccine composition as defined in claim 5 in which the HAV antigen is derived from the HM-175 strain.

7. A vaccine composition according to claim 2 in which the carrier is selected from the group consisting of aluminium hydroxide, aluminium phosphate and tocopherol and an oil in water emulsion.

8. A vaccine composition according to claim 1 or claim 2 wherein the HBsAg antigen is a HBsAg S antigen and the HSV gD antigen is a HSVgDt antigen, further comprising an HAV HM-175 inactivated strain antigen.

* * * * *